(12) United States Patent
Sonnleitner

(10) Patent No.: US 10,321,979 B2
(45) Date of Patent: Jun. 18, 2019

(54) DENTAL IMPLANT SYSTEM

(71) Applicant: Dietmar Sonnleitner, Salzburg (AT)

(72) Inventor: Dietmar Sonnleitner, Salzburg (AT)

( * ) Notice: Subject to any disclaimer, the term of this patent is extended or adjusted under 35 U.S.C. 154(b) by 0 days.

(21) Appl. No.: 15/724,712

(22) Filed: Oct. 4, 2017

(65) Prior Publication Data

US 2019/0099243 A1    Apr. 4, 2019

(51) Int. Cl.
*A61C 8/00* (2006.01)
*A61C 8/02* (2006.01)
*A61F 2/28* (2006.01)

(52) U.S. Cl.
CPC ........... *A61C 8/0006* (2013.01); *A61C 8/008* (2013.01); *A61C 8/0068* (2013.01); *A61C 8/0074* (2013.01); *A61F 2/2846* (2013.01)

(58) Field of Classification Search
CPC ..... A61C 8/006; A61C 8/0074; A61C 8/0068; A61C 8/008; A61F 2/2846
See application file for complete search history.

(56) References Cited

U.S. PATENT DOCUMENTS

| | | | | |
|---|---|---|---|---|
| 4,854,872 A * | 8/1989 | Detsch | ................ | A61C 8/0001 433/173 |
| 5,015,186 A * | 5/1991 | Detsch | ................ | A61C 8/0001 433/173 |
| 5,511,565 A * | 4/1996 | Syers | ................ | A61B 17/8071 128/859 |
| 5,759,033 A * | 6/1998 | Elia | ........................ | A61C 8/00 433/173 |
| 5,899,697 A * | 5/1999 | Lazzara | ................ | A61C 8/008 433/173 |
| 6,012,923 A * | 1/2000 | Bassett | ................ | A61C 8/005 433/172 |
| 6,171,106 B1 * | 1/2001 | Kaneko | ................ | A61C 8/0006 433/173 |
| 6,244,868 B1 * | 6/2001 | Schappert | ............ | A61C 8/0006 433/173 |
| 6,537,070 B1 * | 3/2003 | Stucki-McCormick | ..................... | A61B 17/666 433/173 |
| 7,172,422 B1 * | 2/2007 | Essiger | .............. | A61B 17/8038 433/172 |
| 2001/0032022 A1 * | 10/2001 | Ricci | ................... | A61F 2/30767 623/23.56 |
| 2002/0055700 A1 * | 5/2002 | Ashman | ............... | A61C 8/0006 602/41 |

(Continued)

FOREIGN PATENT DOCUMENTS

KR  10-2011-0111116   10/2011
KR  10-20016-0092794   8/2016
(Continued)

*Primary Examiner* — Nicholas D Lucchesi
(74) *Attorney, Agent, or Firm* — Wenderoth, Lind & Ponack, L.L.P.

(57) ABSTRACT

A dental implant system for bone regeneration of a bone defect site of a jawbone includes an implant which is to be anchored in the jawbone, a film for covering the bone defect site and the implant, a spacer element which, in a fitted position of the dental implant system, is to be arranged between the implant and the film, and an abutment. In the fitted position of the dental implant system, the film is clamped between the spacer element and the abutment, and the spacer element and the abutment are connected by a form-locked connection.

23 Claims, 16 Drawing Sheets

(56) References Cited

U.S. PATENT DOCUMENTS

| | | | | |
|---|---|---|---|---|
| 2003/0013068 | A1* | 1/2003 | Gittleman | A61C 8/005 |
| | | | | 433/173 |
| 2003/0118968 | A1* | 6/2003 | Massoud | A61C 8/0006 |
| | | | | 433/173 |
| 2005/0059864 | A1* | 3/2005 | Fromovich | A61C 8/0033 |
| | | | | 600/201 |
| 2005/0107877 | A1* | 5/2005 | Blain | A61B 17/7071 |
| | | | | 623/16.11 |
| 2005/0192675 | A1* | 9/2005 | Robinson | A61B 17/8071 |
| | | | | 623/23.46 |
| 2006/0008773 | A1* | 1/2006 | Liao | A61C 8/0006 |
| | | | | 433/173 |
| 2008/0044449 | A1* | 2/2008 | McKay | A61B 17/58 |
| | | | | 424/423 |
| 2012/0045735 | A1* | 2/2012 | Drapeau | A61B 17/8085 |
| | | | | 433/172 |
| 2014/0147814 | A1* | 5/2014 | Collins | A61F 2/2803 |
| | | | | 433/215 |
| 2014/0199657 | A1* | 7/2014 | Moon | A61F 2/2803 |
| | | | | 433/173 |
| 2016/0338836 | A1* | 11/2016 | Sonnleitner | A61F 2/2803 |
| 2017/0020634 | A1* | 1/2017 | Sonnleitner | A61C 8/0006 |
| 2017/0143492 | A1* | 5/2017 | Sonnleitner | A61F 2/2846 |

FOREIGN PATENT DOCUMENTS

| | | |
|---|---|---|
| WO | 2013/020216 | 2/2013 |
| WO | 2015/185603 | 12/2015 |

\* cited by examiner

Fig. 4
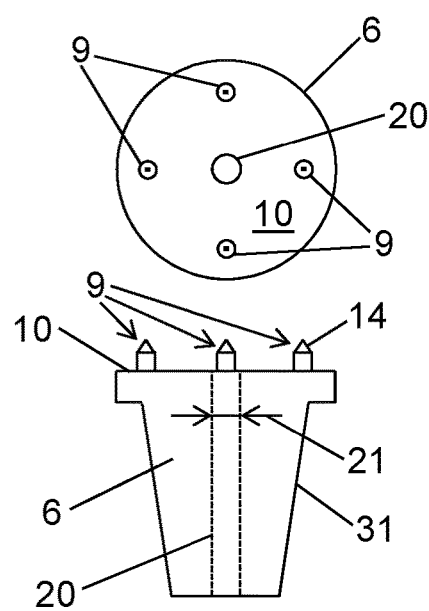
Fig. 6
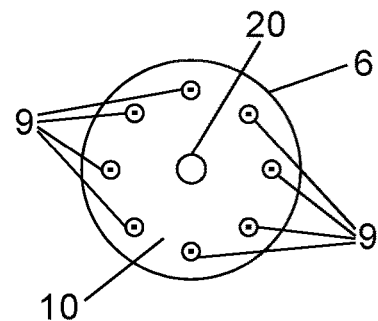
Fig. 7
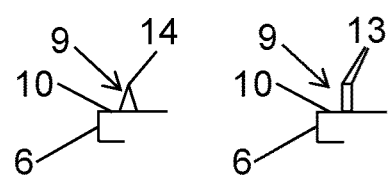
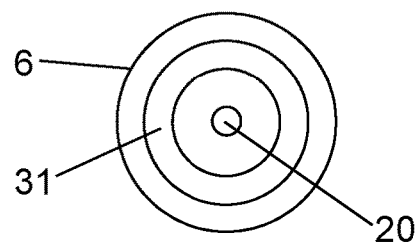
Fig. 5
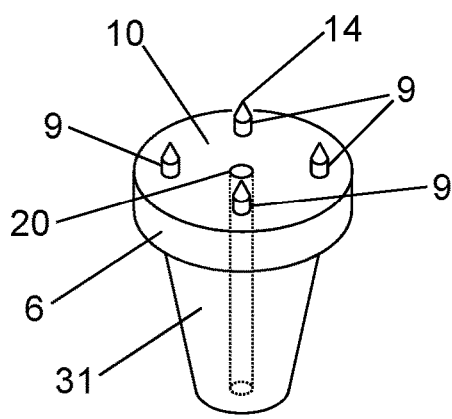

Fig. 19 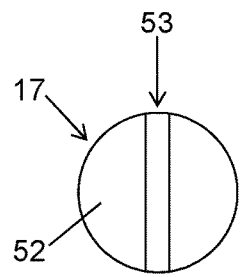 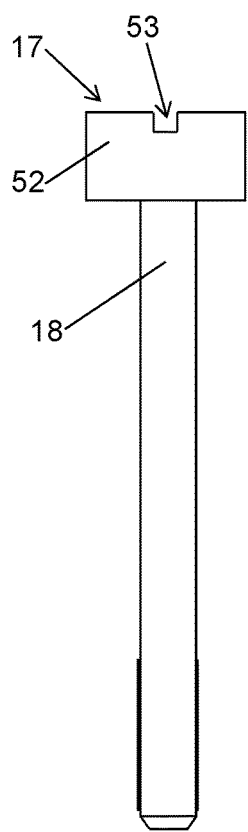
Fig. 20 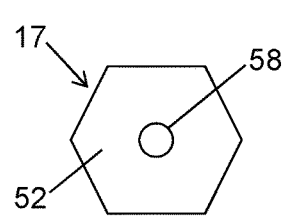 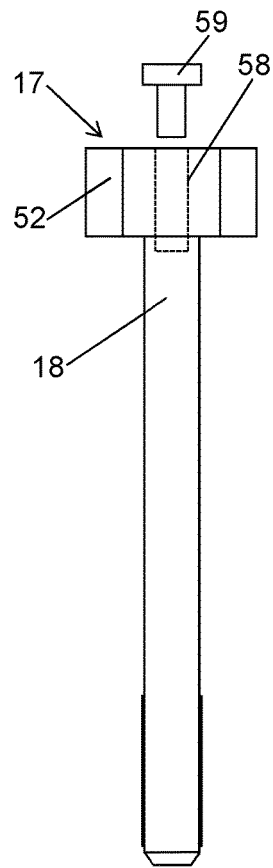
Fig. 21 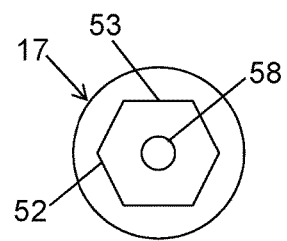 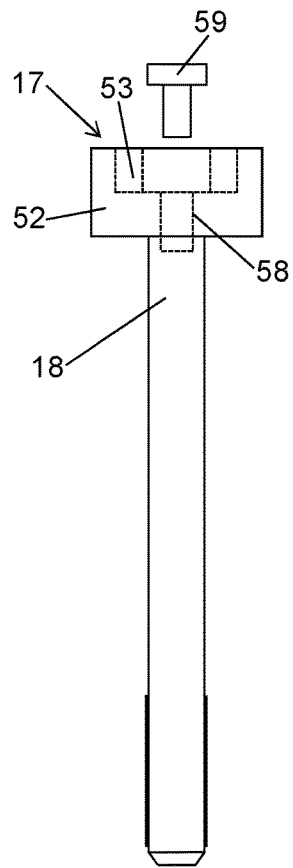

Fig. 26
Fig. 27
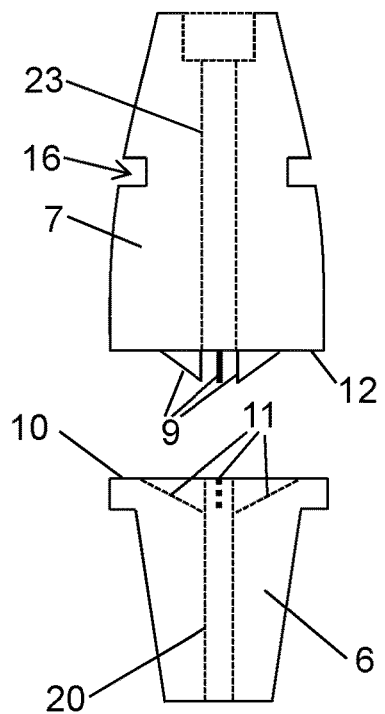
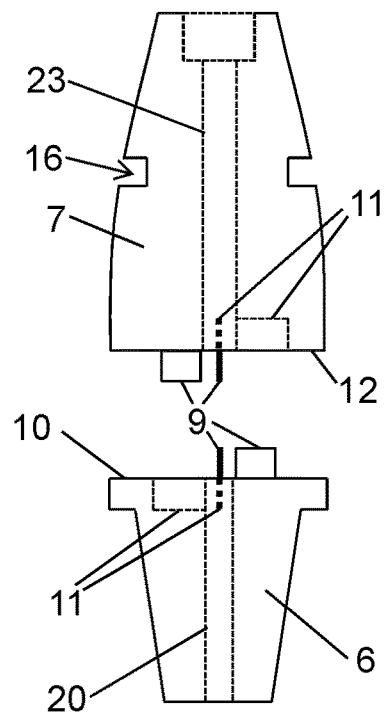

Fig. 28
Fig. 29
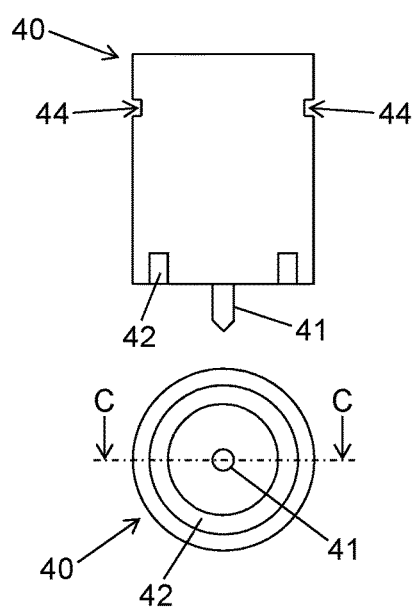
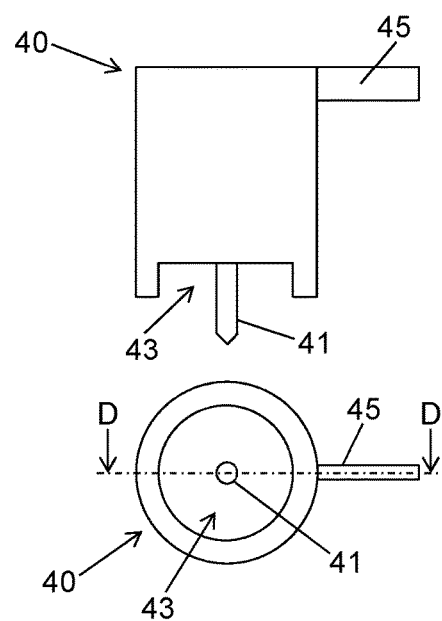
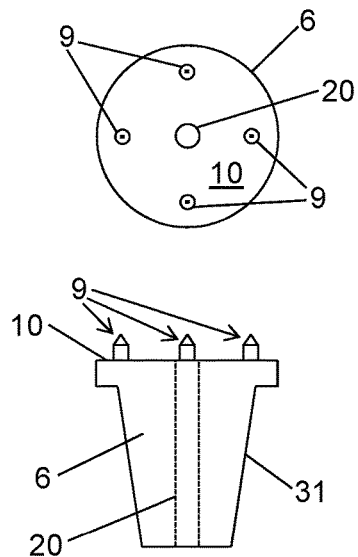
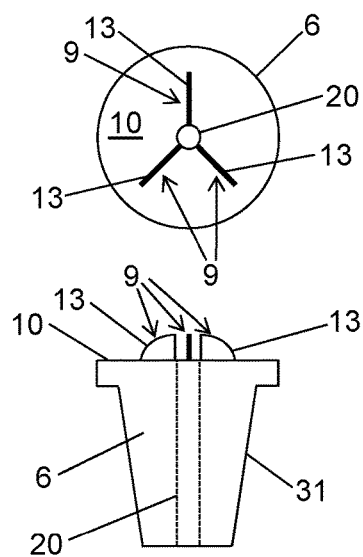

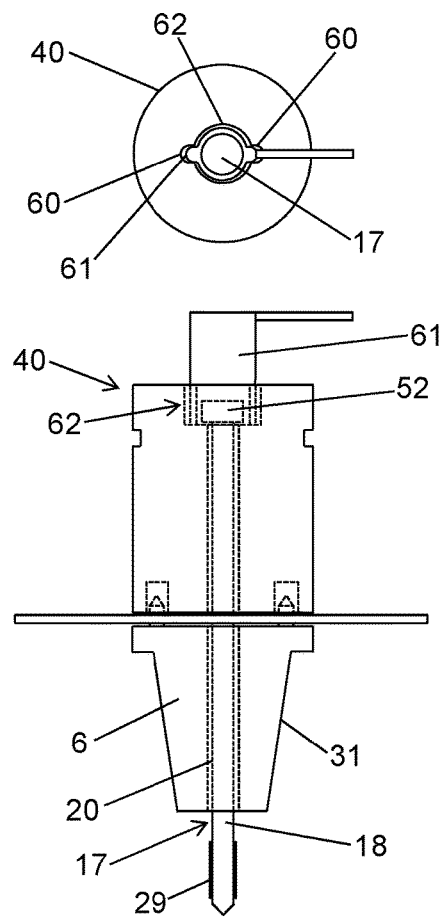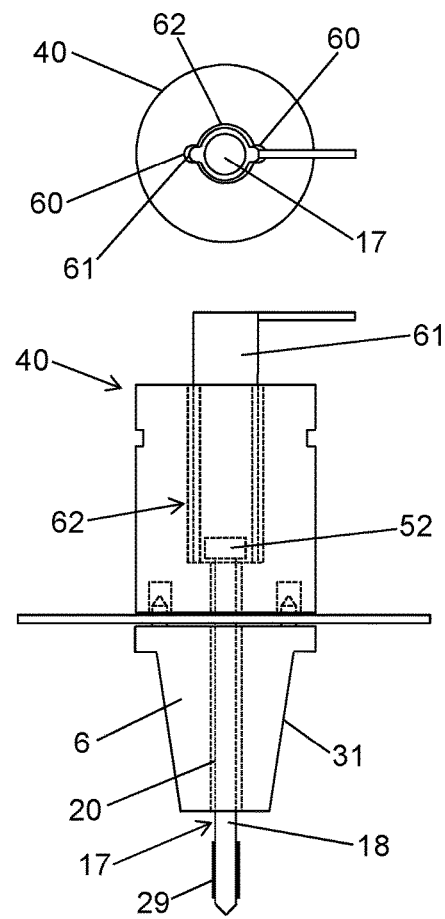

DENTAL IMPLANT SYSTEM

BACKGROUND OF THE INVENTION

1. Field of the Invention

The invention concerns a dental implant system for bone regeneration of a bone defect site of a jawbone including an implant which is to be anchored in the jawbone, a film for covering over the bone defect site and the implant, a spacer element which in a fitted position of the dental implant system is to be arranged between the implant and the film, and an abutment, wherein the film in the fitted position is to be clamped between the spacer element and the abutment. Furthermore, the invention relates to a set comprising a dental implant system and a punch device. The set can also comprise a counter torque wrench or handle.

2. Description of the Related Art

Dental implant systems are already known, using membrane technology, to promote bone regeneration of a bone defect site. Such dental implant systems include an implant which is anchored in the region of the bone defect site in the jawbone, a film or membrane which permits bone regeneration and which is stretched over the bone defect site and thus also over the implant and fixed to the jawbone. That provides between the film and a surface of the bone defect site a cavity in which bone material and in the case of natural teeth also the periodontium can subsequently grow. For advantageous bone regeneration the cavity can also contain bone substitute materials, carriers for drugs, growth factors or other substances which protect and promote healing and bone formation.

Known dental implant systems further include a spacer element that can be arranged between the implant and the film. In the fitted position of a dental implant system in which the components of the dental implant system are arranged and fixed in position at the bone defect site of a jawbone, the provision of a spacer element between the implant and the film which is to be placed over the bone defect site makes it possible to compensate for an unwanted difference in levels between a first level of an implant head at a face end of the implant and a second level of an edge of the bone defect site, in a simple fashion, in dependence on the configuration of the bone defect site. In other words, the spacer element or the part of the spacer element which is arranged between the end face of the implant and the film allows for leveling out the different levels between the end face or top of the implant and the edge of the bone that surrounds the bone defect site. The part of the spacer element which is arranged between the end face of the implant and the film can for example have a height in the range of 0.1-6 mm. By means of the spacer element unwanted crater formation in respect of the film can be avoided by virtue of flexible adaptation to given differences in level between the implant head and the edge of the bone defect site. The spacer element can also be used to support the membrane above the level of the surrounding bone, in order to gain a newly formed vertical bone level with means of vertical bone augmentation.

Before anchoring and arranging a dental implant system at a bone defect site the gum of the patient has to be opened in order to uncover the bone defect site. After anchoring and arranging the dental implant system at the bone defect site the gum is placed over the bone defect site and around the dental implant system and it is sutured. Known dental implant systems include abutments or healing posts in order to be able to provide a channel through the gum of a patient such that a dental prosthesis such as a dental crown can be anchored at the implant (e.g. by cementing or screwing the dental prosthesis onto the dental implant system). Such abutments have different outer diameters, shapes and heights to be adaptable to different thicknesses of soft tissue or gum. An abutment can for example be straight or angled along its longitudinal extension and it can have a shoulder at its base with a height in the range of 0.1-6 mm, wherein the shoulder can correspond to a respective emergence profile of a dental crown to be arranged at the abutment. There are also abutments in the form of a simple sleeve or flat washer. The dental implant system completely or in parts can be made of metal, Zirconia oxide or oxides from any metal or resin like materials.

Depending on the respective configuration of the bone defect site, when using known dental implant systems, when applying the film or membrane, unwanted fold or crater formation can occur, which in turn can lead to an unwanted surface structure in respect of the regenerated jawbone or to loosening of the abutment, as it will not be attached properly and tightly enough to the spacer, thus creating inflammatory reactions with all consequences to the augmented site.

SUMMARY OF THE INVENTION

Therefore the object of the invention is to provide an improved dental implant system for bone regeneration of a bone defect site of a jawbone, which in particular facilitates application of the film at the bone defect site and which permits an improved surface structure for the regenerated bone material.

According to the invention it is therefore provided that in the fitted position the spacer element and the abutment are connected by means of a form-locked connection. By the provision of a form-locked connection for connecting the abutment with the spacer element in combination with the fact that the film is to be clamped between the spacer element and the abutment an unwanted folding, turning or creasing of the film can be avoided, as the film is not turned or creased when being fixed in its stable position.

In a preferred embodiment it can be provided that the form-locked connection is rotationally locked. This is in particular advantageous when the spacer element is arranged in a fixed position relative to the implant. In such a case the abutment will not be able to rotate relative to the spacer element and the film clamped in between the spacer element and the abutment will not be folded, turned or creased.

A particularly preferred embodiment provides that the form-locked connection is configured such that the spacer element has at least one projection projecting from a spacer surface of the spacer element that faces towards the film in the fitted position, wherein the abutment has at least one recess in an abutment surface of the abutment that faces towards the film in the fitted position, and/or the abutment has at least one projection projecting from the abutment surface, wherein the spacer element has at least one recess in the spacer surface, wherein in the fitted position the at least one recess corresponds to the at least one projection such that the at least one projection projects through the film and into the at least one recess. Preferably, at least one projection surface of the at least one projection in the fitted position abuts against an inner wall of the at least one recess. Such a configuration enables a connection between the spacer element and the abutment that is form-locked as well as rotationally locked.

In a preferred embodiment it can be provided that the at least one projection has at least one sharp edge or tip in order to facilitate the penetration of the at least one projection through the film.

It can be provided that the at least one projection is in the form of a pin or ledge.

It can also be provided that the at least one projection has a conical, tapered, rectangular or triangular outer shape.

In a preferred embodiment a plurality of projections can be provided. This allows a more reliable connection.

In order to simplify connecting the abutment with the spacer element it can be provided that there are more recesses than projections. By this, connecting the abutment with the spacer element is not only possible in one single defined orientation of the abutment relative to the spacer element in a direction of rotation around a rotation axis but rather there are several possible orientations of the abutment relative to the spacer element in which a connection is possible.

In a preferred embodiment it can be provided that in the fitted position the implant and the spacer element are connected by means of a form-locked spacer connection. Preferably, the form-locked spacer connection is rotationally locked. Thus, the spacer element can be arranged in rotationally locked relationship on the implant. A rotationally locked arrangement of the spacer element on the implant ensures that the spacer element can not be rotated relative to the implant.

There are many different dental implant systems on the market which differ in the way in which elements of the dental implant system can be connected to the implant. For example, some dental implant systems have implants with a polygonal recess into which elements (e.g. abutments) with corresponding polygonal projections can be fitted. Similarly, there are implants with polygonal projections onto which elements with corresponding polygonal recesses can be fitted.

In one example of a spacer connection the spacer connection can comprise spacer projections projecting from the spacer element towards the implant, wherein the spacer projections can be inserted into corresponding implant recesses of the implant. Generally, the spacer element can be configured with projections or recesses corresponding to the respective implant onto which the spacer element is to be fitted in order to achieve a form-locked and preferably also rotationally locked spacer connection.

In a preferred embodiment it can be provided that the abutment has at least one tool reception. The tool reception serves to receive a tool like for example a torque wrench (counter torque wrench) with which the abutment can be held against the torque, when it is screwed or anchored to the implant. The tool reception can be in the form of recesses in an outer shell surface of the abutment. The tool reception can also be in the form of a slit-shaped or polygonal recess in an end face of the abutment.

A particularly advantageous embodiment of the invention is that wherein the dental implant system further comprises a fixing screw for positionally stable fixing of the film relative to the implant, wherein in the fitted position a screw bolt of the fixing screw projects through the abutment, the film and the spacer element, wherein the screw bolt is to be screwed into a threaded bore in the implant. By this, the elements of the dental implant system are clamped between a screw head of the fixing screw and the implant. It can preferably be provided that at a screw head surface which in the fitted position is towards the abutment the screw head is provided with a friction-reducing coating, preferably with a Teflon or gold coating.

In a preferred embodiment it can be provided that the spacer element for passing the screw bolt therethrough has a through bore of a bore diameter larger than an outside diameter of the screw bolt. It can also be provided that the abutment for passing the screw bolt therethrough has an through hole of a hole diameter which is larger than the outside diameter of the screw bolt. In that way the screw bolt projects through the spacer element and the abutment without making contact therewith and is not in engagement with the spacer element or the abutment during screwing to the threaded bore in the implant.

In that case the screw bolt having a bolt thread (e.g. in the form of a male thread) projects through the abutment, the film and the spacer element (with the film to be clamped between the abutment and the spacer element) and can be screwed to a corresponding thread (e.g. in the form of a female thread) in the threaded bore of the implant. Due to the fact that the screw bolt projects through the abutment and the spacer element without engagement therewith neither the abutment nor the spacer element will rotate with the fixing screw during the positionally stable fixing of the film, whereby the film is also not turned or creased. The abutment, the film and the spacer element are clamped in an axial direction (with respect to the screw bolt or threaded bore) between the screw head and the implant by screwing the fixing screw into the threaded bore in the implant. However, neither of these elements will rotate by screwing the fixing screw. Thereby, unwanted folding of the film can be avoided in the region of the film in which the screw bolt projects through the film, as the film is not turned or creased when being fixed in its stable position.

Further, a rotationally locked arrangement of the spacer element on the implant and a rotationally locked arrangement of the abutment on the spacer ensure that the abutment and the spacer element are not also rotated with the fixing screw during fixing of the film relative to the implant, that is to say while the fixing screw is being screwed to the implant. Such rotationally locked connections provide a rotation-preventing means for preventing unwanted folding when the dental implant system and the film are being fixed.

A particularly advantageous embodiment of the invention is that in which the spacer element is of a substantially hollow cylindrical shape, preferably in the form of a substantially tubular sleeve. In that case the spacer element can be in the form of a spacer sleeve which is particularly easy to manufacture.

It can also be provided that the spacer element is substantially conical or frustoconical. In that way in particular an enlarged contact surface for the film on the spacer element can be formed and the anatomical shape of a natural root can be simulated.

In a preferred embodiment it can be provided that on a spacer surface of the spacer element that faces towards the film in the fitted position and/or on an abutment surface of the abutment that faces towards the film in the fitted position is at least one extension, preferably of a substantially thorn-like configuration. Such at least one extension (which in the fitted position of the dental implant system projects into the film) is for positional fixing of the film relative to the spacer element and/or the abutment. That can prevent the film from turning or creasing.

In a particularly preferred embodiment it can be provided that the film is substantially completely resorbable or non-resorbable. If the film or membrane overall is completely resorbable in the body by being broken down for example by hydrolysis in the body there is no need to perform a further operation for removal of the film after bone regeneration has occurred.

Generally, the film can be a standard single layer film.

A particularly advantageous embodiment is that in which the film is a preferably pre-bonded multi-layer film which includes a shaping forming layer for shaping the film to the bone defect site and at least one cover layer for covering the bone defect site, wherein the forming layer and the at least one cover layer are substantially completely resorbable. In that case the film includes a shaping forming layer which serves for shaping the film to the bone defect site and by which a cavity can be formed between the bone defect site and the film so that bone growth can occur in that cavity. The cavity is maintained by the space-forming and space-maintaining forming layer until the cavity is filled up by growing bone material. In addition the film of this embodiment includes at least one cover layer for covering the bone defect site. That cover layer which for example can be in the form of a membrane serves for covering and sealing off the bone defect site to prevent soft tissue from passing into the bone defect site. In order further to improve fitting of the film and the sealing of the bone defect site the at least one cover layer can also be such that it adheres to a gum surrounding the bone defect site. The individual layers of such a pre-bonded film (forming layer and at least one cover layer) can be mechanically and/or chemically bonded together.

In a preferred embodiment it can be provided that the forming layer and the at least one cover layer are substantially completely resorbable in different periods of time. For example, the design of the forming layer and the at least one cover layer makes it possible to provide that the forming layer is resorbed more quickly than the at least one cover layer. Generally, differing degrees of resorbability of the forming layer and the at least one cover layer give great degrees of freedom in the design of the film in relation to resorbability.

It can be provided that the film can be substantially completely resorbed in a period of between about 3 and 12 months, preferably between about 4 and 6 months. That is the period of time within which bone regeneration occurs in the normal case.

To permit good shaping to the bone defect site and stable cavity formation between the film and the bone defect site it can be provided that the forming layer is stiffer than the at least one cover layer. The higher degree of stiffness of the forming layer serves to form a cavity for bone construction and also to maintain that cavity for the period required for bone regeneration. Once again, good coverage and sealing of the bone defect site can be achieved by the at least one cover layer being of lesser stiffness in comparison with the forming layer.

Preferably it can be provided that the forming layer, possibly together with the at least one cover layer, is adapted to be mechanically and/or thermally and/or chemically deformable. Thus in particular the forming layer can be in the form of a layer which is substantially stable in shape and which can be deformed under a mechanical, thermal or chemical influence and which after such deformation again enjoys adequate stability in respect of shape to maintain the cavity to be formed for bone growth, for the required period of time. The at least one cover layer can be flexible and preferably elastic to permit good coverage and sealing of the bone defect site.

In that case mechanical deformation can be effected for example by bending with a tongs. That is a suitable shaping method in particular for comparatively thin forming layers (for example in the range of between about 0.10 mm and about 0.3 mm). For thicker forming layers (for example thicker than about 0.3 mm) thermal deformation of the layer can be appropriate for the shaping operation. Suitable thermal deformation can be achieved in that case for example by means of a thermal bar with a hot tip or surface, by way of heated prefabricated models or in a hot water bath with a sterile saline solution. Industrial preforming and -shaping of the membrane is another option.

For good resorbability of the proposed film it can be provided that the at least one cover layer at least partially and preferably substantially completely comprises a bioresorbable collagen material. In that case it can be provided that the bioresorbable collagen material includes type-I-collagen and/or type-III-collagen. The collagen material can for example originate from bovine Achilles tendon or from the pericard.

For good resorbability of the proposed film it can also be provided that the forming layer at least partially and preferably substantially completely comprises a bioresorbable polymer material. The bioresorbable polymer material can also be a copolymer material.

A particular variant provides that the bioresorbable polymer material includes lactic acid, preferably L-lactic acid, and/or derivatives thereof. It is advantageous in that case if the proportion of lactic acid in the bioresorbable polymer material is at least 70%, preferably between about 80% and 95%, particularly preferably substantially about 82%.

In addition it can be provided that the bioresorbable polymer material includes glycolic acid. It is advantageous in that respect if the proportion of glycolic acid in the bioresorbable polymer material is at most 30%, preferably between about 15% and 20%, particularly preferably substantially about 18%. Depending on the respective composition of the forming layer it can be provided that the forming layer is substantially stable in respect of shape and is nonetheless substantially completely resorbable.

In a further preferred embodiment it can be provided that the forming layer and the at least one cover layer are of different surface areas. In that respect it can be provided that the forming layer is of a smaller surface area than the at least one cover layer. If the at least one cover layer covers over the forming layer by virtue of its smaller surface area it is possible to achieve particularly good coverage and thus also sealing of the bone defect site.

Preferably it can be provided that the at least one cover layer and/or the forming layer is or are of a substantially flat configuration throughout. A contour for the film, which is advantageous for shaping to the bone defect site, can be achieved for example by suitably cutting the film.

It is particularly advantageous however if the forming layer for shaping to the bone defect site has a shape structure. In that case it can be provided that the shape structure has at least portion-wise a convexly and/or concavely curved edge and/or at least portion-wise a convexly and/or concavely curved shape. In other words the shape structure can have for example areal—convexly and/or concavely curved—projections and thus a convexly and/or concavely curved edge. Alternatively or additionally the shape structure as a whole can also be of a correspondingly convexly and/or concavely curved shape.

It is particularly advantageous if the shape structure has at least one strut-shaped shaping element. The strut-shaped or tab-shaped shaping elements can be shaped in a hoop-like configuration over the bone defect site and permit any cavity shape to be produced.

A particularly advantageous embodiment of the invention is that in which the shape structure is of a substantially grid-shaped configuration. The grid-shaped structure in that case forms a reinforcing grid which permits the formation of a plurality of any desired cavity shapes.

It can also be provided that the shape structure is formed by at least one reinforcement of the forming layer. Particularly if the forming layer is applied in the form of a hardening liquid or a hardening gel to the at least one cover layer it is desirable if the shape structure can be achieved merely by applying more liquid or gel in the region of the shape structure. In that case for example the shape structure can be of differing thicknesses.

A particular variant provides that the film has a carrier layer for at least one substance which is arranged or which is to be arranged thereon. The substances arranged or to be arranged on the carrier layer can be drugs, growth factors or other substances for protecting and promoting healing and bone formation. The carrier layer can preferably be arranged at a side of the film, that is to face towards the bone defect site, and can at least partially and preferably substantially completely comprise a bioresorbable collagen material.

It can also be provided that appropriate substances are applied directly to the forming layer and/or the at least one cover layer. It can also be provided that the side or surface of the film, that is to face towards a bone defect site, itself serves as a carrier for the above-described substances, by for example that side or surface of the film having a suitable roughness.

Depending on the respective situation of use the film or membrane can also be provided in pre-cut and/or pre-shaped fashion. In that case for example a desired cut configuration and/or a desired 3D deformation of the film can be effected in accordance with data processing-aided planning.

In general the individual components of the proposed dental implant system, depending on the respective situation of use, can be planned and produced, for example milled, individually in a data processing-aided procedure.

According to a further aspect of the invention a set is provided, wherein the set comprises a dental implant system as proposed and a punch device for punching and pressing the film onto the spacer element in order to facilitate the arrangement of the film on the spacer element.

Preferably, the punch device has a punch thorn projecting from the punch device in order to punch the film when the punch device is arranged on and pressed against the spacer element. Another option is a screw bolt with which the punch device can be screwed onto the spacer or onto the implant, thus perforating the film. Thereby, the thread of the bolt can engage the internal bore thread of the implant.

In an embodiment, wherein the form-locked connection for connecting the spacer element and the abutment comprises at least one projection to be engaged into a corresponding recess, it can preferably be provided that the punch device has an annular punch groove or a punch space in the form of a cylindrical bore, wherein the at least one projection can be introduced into the annular punch groove or the punch space when the punch device is arranged on top of the spacer element and pressed against the spacer element. By this, the penetration of the at least one projection through the film can be facilitated.

BRIEF DESCRIPTION OF THE DRAWINGS

Further details and advantages of the present invention are described hereinafter by means of the specific description. In the drawing:

FIG. 4 shows another example of a spacer element in a top view, a side view and a bottom view, FIG. 5 shows the spacer element of FIG. 4 in a perspective view, FIG. 6 shows a top view of another example of a spacer element, FIG. 7 shows examples of outer shapes of projections, FIG. 19 shows a top view and a side view of a fixing screw, FIG. 20 shows a top view and a side view of another example of a fixing screw, FIG. 21 shows a top view and a side view of another example of a fixing screw, FIG. 26 shows another example of an abutment and a corresponding spacer element, FIG. 27 shows another example of an abutment and a corresponding spacer element, FIG. 28 shows a sectional side view and a bottom view of an example of a punch device as well as a top view and a side view of a spacer element, FIG. 29 shows a sectional side view and a bottom view of a further example of a punch device as well as a top view and a side view of a spacer element, FIG. 30 shows a top view and a side view of another example of a punch device, FIG. 31 shows a top view and a side view of another example of a punch device.

DETAILED DESCRIPTION OF THE INVENTION

Figure 1:
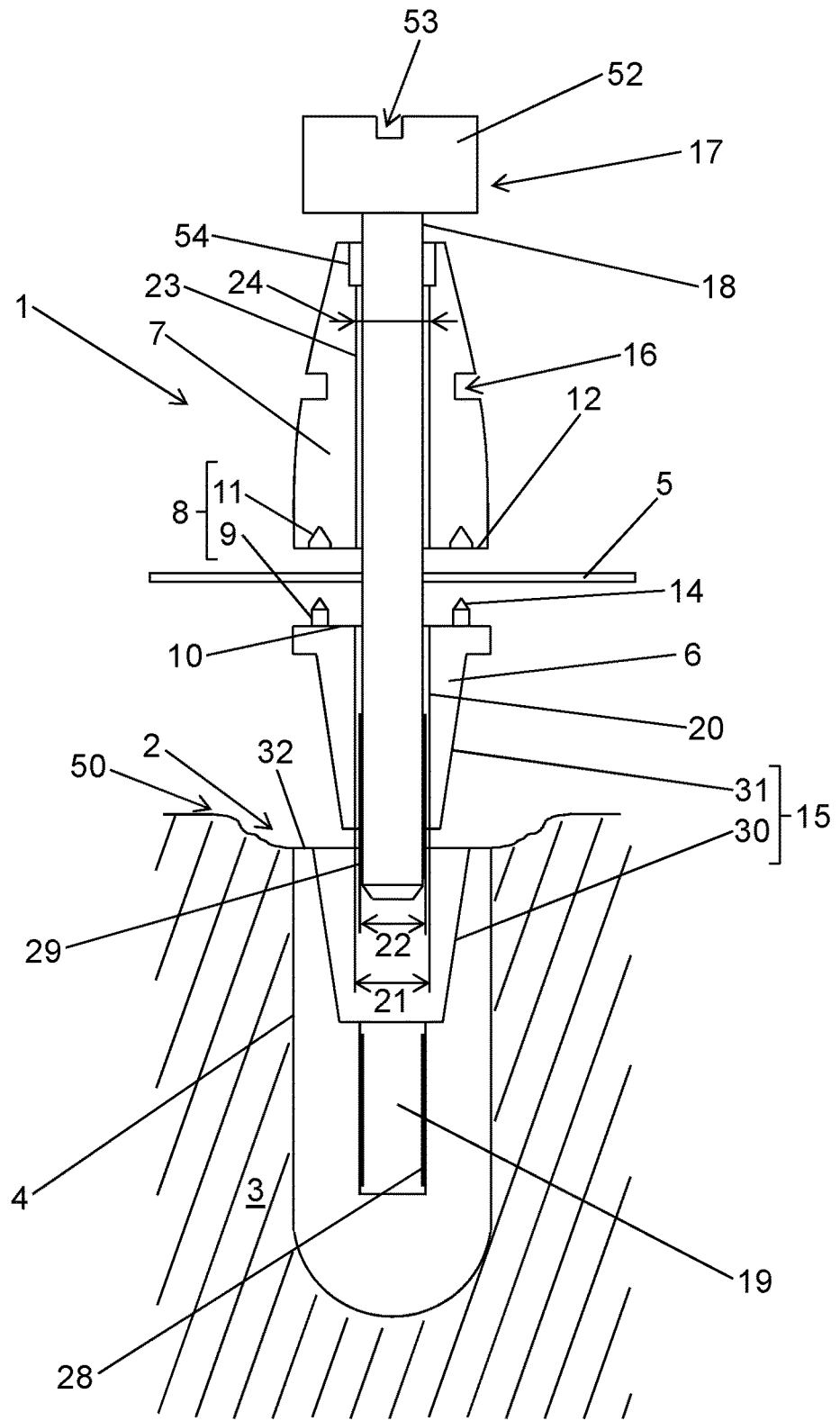
FIG. 1 shows a sectional view through a dental implant system arranged at a bone defect site of a jawbone.
Figure 2:
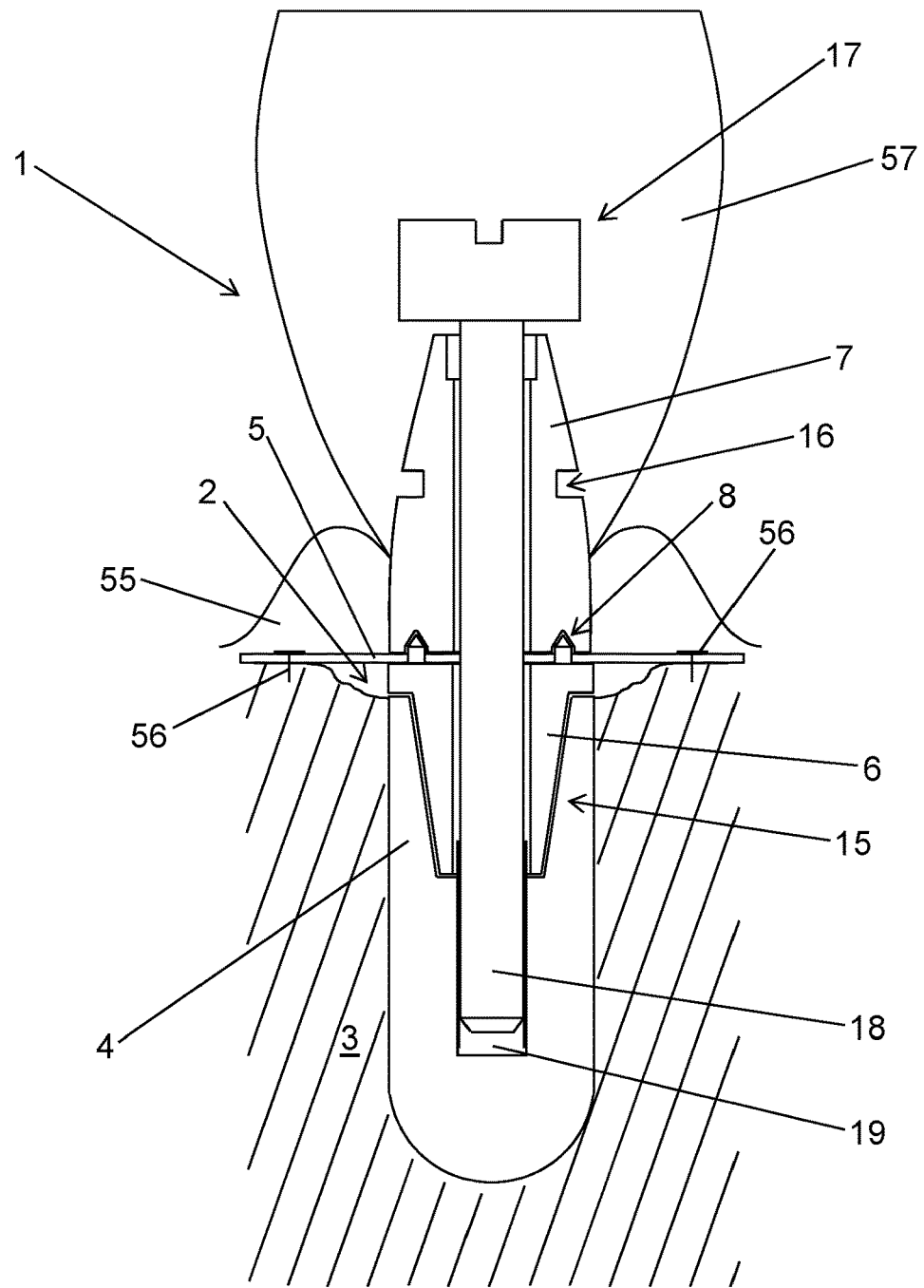
FIG. 2 shows a sectional view through the dental implant system of FIG. 1 in its fitted position.

FIG. 1 shows a sectional view through a dental implant system 1 arranged at a bone defect site 2 of a jawbone 3 and FIG. 2 shows a sectional view through the dental implant system 1 in its fitted position, that means in a position in which the components of the dental implant systems 1 are arranged and fixed in position at the bone defect site 2 of the jawbone 3.

The dental implant system 1 comprises an implant 4 which is to be anchored in the jawbone 3 in the region of the bone defect site 2. To permit bone regeneration in the region of the bone defect site 2 a membrane or film 5 is placed over the bone defect site 2 and thus also over the implant 4 and fixed to the jawbone 3 to form a cavity between the bone defect site 2 and the film 5, in which the jawbone 3 can regenerate. Depending on the respective configuration of a bone defect site 2 and anchorage of the implant 4 however there can be differences in level between a first level of the implant head 32 of the implant 4 and a second level of an edge 50 of the bone defect site 2. In order to achieve uniform bone growth and a desired surface for the regenerated jawbone 3 in spite of such a difference in level there is provided a spacer element 6 which is arranged between the implant 4 and the film 5 to compensate for precisely that difference in level.

The implant 4 comprises an implant adapter 30 and the spacer element 6 comprises a spacer adapter 31 which corresponds to the implant adapter 30. When the spacer element 6 is arranged on the implant 4, the implant adapter 30 and the spacer adapter 31 constitute a form-locked spacer connection 15. The spacer adapter 31 engages into the corresponding implant adapter 30 such that the spacer element 6 and the implant 4 are connected in a form-locked way. Preferably, the form-locked spacer connection 15 is also rotationally locked. In this way, when the spacer element 6 is connected with the implant 4 by means of the spacer connection 15 the spacer element 6 will not be able to rotate relative to the implant 4. This allows a more stable and reliable dental implant system 1.

With the spacer element 6 uniform coverage of the bone defect site 2 with the film 5 can be achieve, without for example unwanted folding or cratering occurring in the film 5. The part of the spacer element 6 which is arranged between the implant head 32 of the implant 4 and the film 5 can have a conical or frustoconical peripheral surface, which provides an enlarged contact surface for the film 5 and which can simulate the anatomical root shape.

In the example shown the film 5 is anchored to the jawbone 3 by means of suitable fixing devices 56. The fixing devices 56 can involve for example metal or resorbable nails, pins or screws which are fixed through the film 5 to the jawbone 3. Alternatively the film 5 can also be glued to the jawbone 3.

The dental implant system 1 further comprises an abutment 7 which holds open a passage through the gum 55 of the patient to the oral cavity. After the dental implant system 1 is arranged at the bone defect site 2 in its fitted position the gum 55 is arranged around the abutment 7. Further, the abutment 7 can form the basis for a dental prosthesis 57 (e.g. an artificial tooth) to be fixed (cemented or screwed) on the abutment 7.

In the fitted position, the film 5 is clamped between the spacer element 6 and the abutment 7 and the spacer element 6 and the abutment 7 are connected by means of a form-locked connection 8.

In the example shown, the form-locked connection 8 is configured such that the spacer element 6 has projections 9 projecting from a spacer surface 10 of the spacer element 6 that faces towards the film 5 in the fitted position and the abutment 7 has recesses 11 in an abutment surface 12 of the abutment 7 that faces towards the film 5 in the fitted position, wherein in the fitted position the recesses 11 correspond to the projections 9 such that the projections 9 project through the film 5 and into the recesses 11. In order to facilitate the penetration of the projections 9 through the film 5 each of the projections 9 has a sharp tip 14.

The abutment 7 of the shown example further has a tool recess 54 and tool receptions 16. By means of the tool recess 54 or the tool receptions 16 a tool can be brought into engagement with the abutment 7 in order to hold the abutment 7 in position during fixing of the dental implant system 1 by screwing a fixing screw 17 into the implant 4. In case the recess 54 is used for holding the abutment 7 in position the screw head 52 of the fixing screw 17 is smaller than the recess 54 or top entrance of the abutment 7, in order to be able to interfere. If the form-locked spacer connection 15 is also rotationally locked and the form-locked connection 8 is also rotationally locked the implant 4 cannot be disanchored or further screwed into the jawbone 3 by rotating the abutment 7 with the tool that is in engagement with abutment 7 (e.g. a counter torque device). Such tool could for example be a torque wrench which provides the possibility to define a maximum torque value without rotating the implant.

In order to fix the dental implant system 1 in its fitted position, the dental implant system 1 shown in the example further comprises a fixing screw 17 for positionally stable fixing of the film 5 relative to the implant 4, wherein in the fitted position a screw bolt 18 of the fixing screw 17 projects through the abutment 7, the film 5 and the spacer element 6, wherein the screw bolt 18 is to be screwed into a threaded bore 19 in the implant 4.

In the example shown the screw bolt 18 of the fixing screw 17 has a screw thread 29 (e.g. in the form of a male thread) and the threaded bore 19 of the implant 4 has a bore thread 28 (e.g. in the form of a female thread) which corresponds to the screw thread 29. The screw bolt 18 has an outside diameter 22. The abutment 7 has a through hole 23 of a hole diameter 24 larger than the outside diameter 22 of the screw bolt 18 of the fixing screw 17 and the spacer element 6 has a through bore 20 of a bore diameter 21 larger than the outside diameter 22 of the screw bolt 18 of the fixing screw 17.

For positionally stable fixing of the film 5 the screw bolt 18 of the fixing screw 17 is passed through the through hole 23 in the abutment 7, through the film 5 or a corresponding hole in the film 5 and through the through bore 20 in the spacer element 6 and screwed to the threaded bore 19 in the implant 4 by means of a tool engaging into a head recess 53 in a screw head 52 of the fixing screw 17. As both the hole diameter 24 of the through hole 23 in the abutment 7 and the bore diameter 21 of the through bore 20 in the spacer element 6 are larger than the outside diameter 22 of the screw bolt 18, the male thread of the screw bolt 18 is not in engagement with the abutment 7 during screwing of the fixing screw 17 whereby the abutment 7 does not also rotate with the fixing screw 17. Similarly, the male thread of the screw bolt 18 is also not in engagement with the spacer element 6 during screwing of the fixing screw 17 whereby the spacer element 6 does not also rotate with the fixing screw 17. In that way it is possible to prevent the film 5 from also turning while it is being fixed in a stable position by clamping it between the abutment 7 and the spacer element 6 whereby as a further consequence unwanted folding of the film 5 in the clamping region does not occur. In order to reduce friction between the screw head 52 of the fixing screw 17 a screw head surface of the screw head 52 of the fixing screw 17, that faces towards the abutment 7, can be provided with a friction-reducing coating, for example with a Teflon or gold coating.

Figure 24:
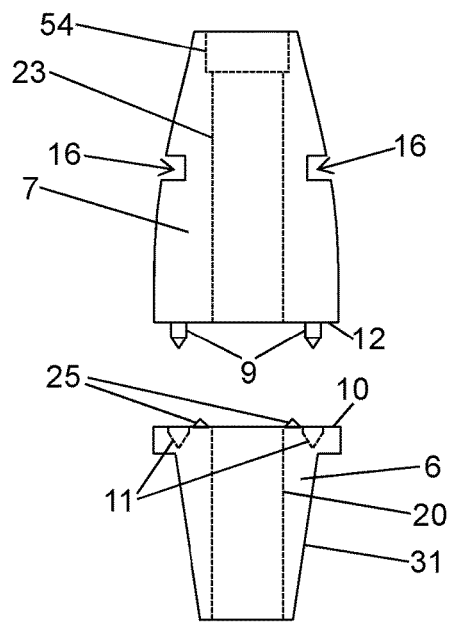
FIG. 24 shows another example of an abutment and a corresponding spacer element.
Figure 25:
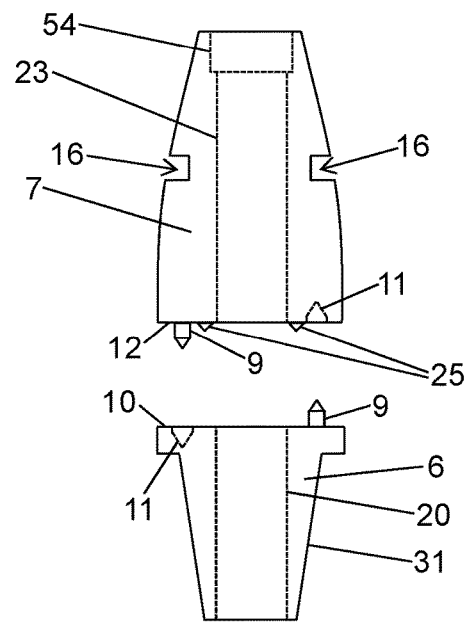
FIG. 25 shows another example of an abutment and a corresponding spacer element.

The general procedure for arranging the components of a proposed dental implant system 1 and for bringing the dental implant system 1 into its fitted position is as follows, wherein the following steps are described with respect to the dental implant system 1 according to FIG. 1 and its fitted position according to FIG. 2:

- anchor the implant 4 in the bone defect site 2 of a jawbone;
- arrange the spacer element 6 on the implant 4, wherein the spacer element 6 and the implant 4 are connected in a form-locked and preferably also rotationally locked way by means of a form-locked spacer connection 15;
- fix the shaped film 5 to the jawbone 3 at its alveolar bone base;
- fill in the bone defect site 2 with bone and/or bone substitutes;
- arrange the film 5 on the spacer element 6 and on the jawbone 3 around the bone defect site 2 and press the film 5 against the spacer element 6 (optionally by using a punch device 40 as for example shown in FIG. 24 or 25), wherein the projections 9 penetrate through the film 5, wherein a stable positioning of the film 5 relative to the implant 4 is achieved;
- optionally fix the film 5 on the jawbone 3 around the bone defect site 2 with additional fixing devices 56;
- arrange the abutment 7 on the film 5, wherein the abutment 7 and the spacer element 6 are connected in a form-locked and preferably also rotationally locked way by means of a form-locked connection 8 (in the shown example the form-locked connection 8 is provided by the projections 9 which project from the spacer element 6 through the film 5 and which engage into recesses 11 in the abutment 7);
- use a counter torque device to avoid unwanted rotation of the implant 4;
- pass the screw bolt 18 of the fixing screw 17 through the abutment 7, the film 5 and the spacer element 6 and screw the screw bolt 18 to the threaded bore 19 in the implant 4, wherein the abutment 7, the film 5 and the spacer element 6 are clamped between the screw head 52 of the fixing screw 17 and the implant 4, wherein the film 5 is clamped between the spacer element 6 and the abutment 7;
- close the wound;
- fix a temporary crown if this is possible under the rules of immediate loading.

Figure 3:
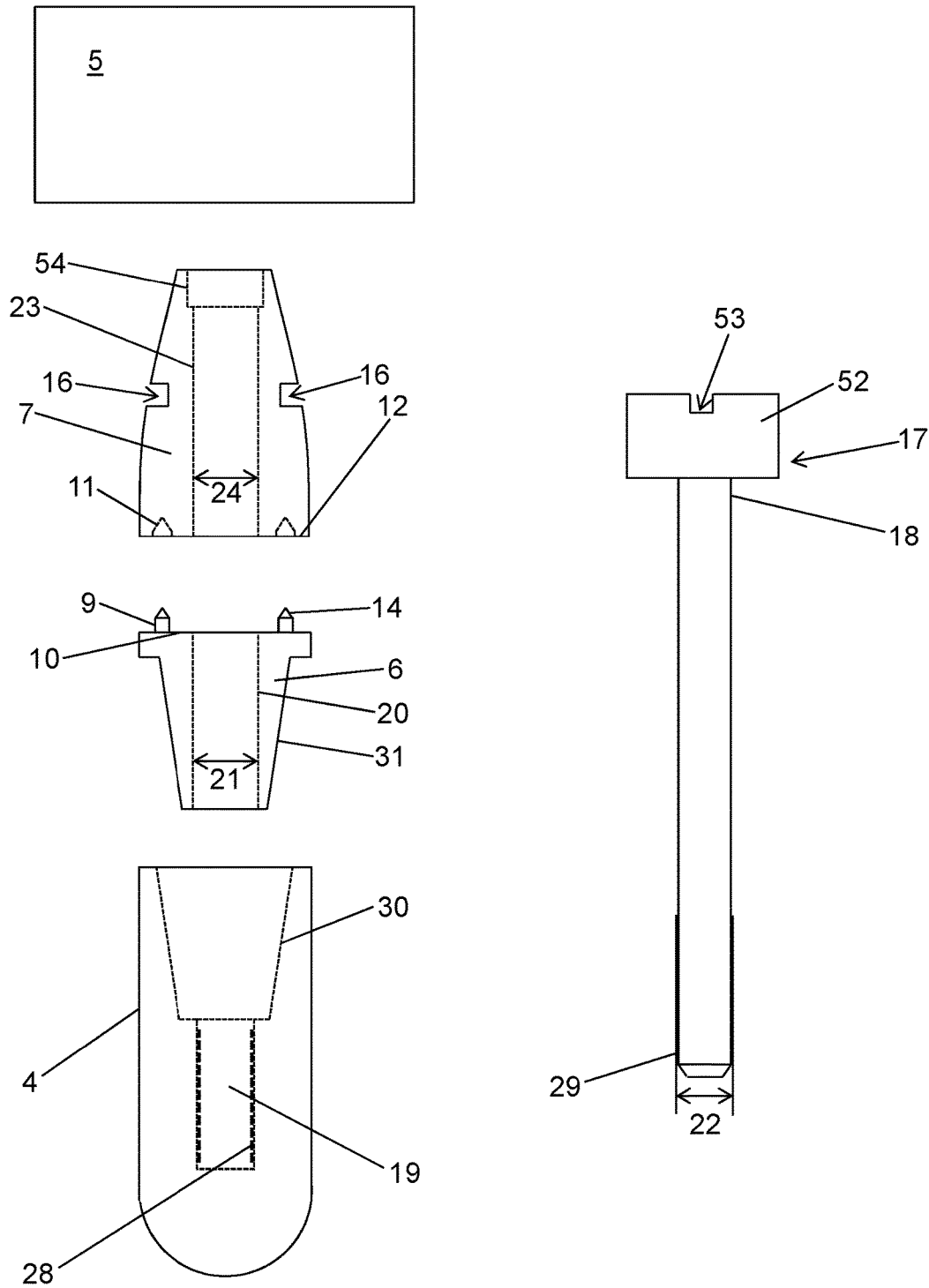
FIG. 3 shows the components of the dental implant system of FIG. 1.

FIG. 3 shows the components film 5, abutment 7, spacer element 6, implant 4 and fixing screw 17 of the dental implant system 1 according to FIG. 1 separated from each other. The film 5 is shown in a top view and the abutment 7, the spacer element 6, the implant 4 and the fixing screw 17 are shown in side views.

FIG. 4 shows another example of a spacer element 6 in a top view, a side view and a bottom view and FIG. 5 shows the spacer element 6 according to FIG. 4 in a perspective view. Compared with the spacer element 6 according to FIG. 3, the spacer element 6 of FIG. 4 has a through bore 20 with a smaller bore diameter 21. On the spacer surface 10 the spacer element 6 has four projections 9, each equipped with a sharp tip 14 in order to facilitate the penetration of the projections 9 through the film 5.

FIG. 6 shows a top view of another example of a spacer element 6. The spacer element 6 shown has eight projections 9 projecting from the spacer surface 10.

FIG. 7 shows examples of outer shapes of projections 9 projecting from the spacer surface 10. Shown are a triangular outer shape and a rectangular outer shape of the projections 9. The triangular projection 9 is equipped with a sharp tip 14 and the rectangular projection 9 is equipped with two sharp edges 13.

Figure 8:
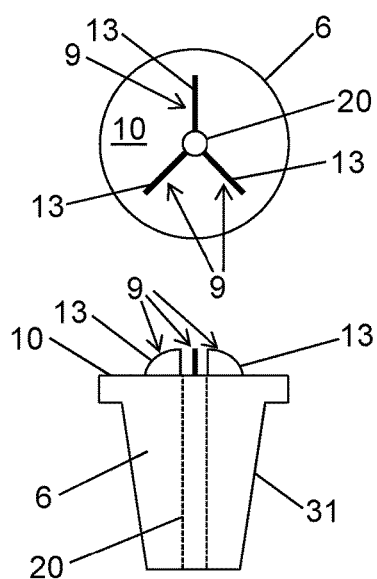
FIG. 8 shows another example of a spacer element in a top view, a side view and a bottom view.
Figure 9:
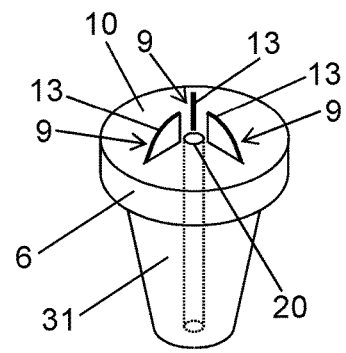
FIG. 9 shows the spacer element of FIG. 8 in a perspective view.

FIG. 8 shows another example of a spacer element 6 in a top view, a side view and a bottom view and FIG. 9 shows the spacer element 6 according to FIG. 8 in a perspective view. In this example, the spacer element 6 has three projections 9 in the form of curved ledges. The projections 9 extend from an area around the through bore 20 radially outwards and each of the projections 9 is equipped with a sharp edge 13.

Figure 10:
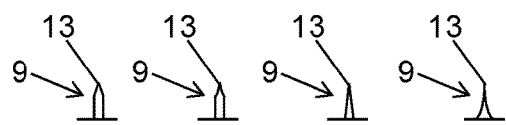
FIG. 10 shows examples of outer shapes of cross-sections of projections in the form of ledges.

FIG. 10 shows examples of outer shapes of cross-sections of projections 9 in the form of ledges projecting from the spacer surface 10. Each of the projections 9 shown is equipped with a sharp edge 13.

Figure 11:
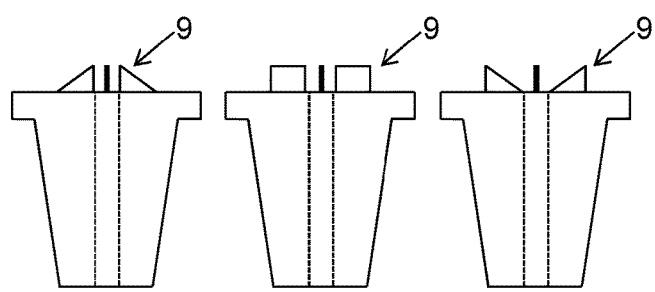
FIG. 11 shows examples of outer edges of projections in the form of ledges.

FIG. 11 shows examples of outer edges of projections 9 in the form of ledges projecting from the spacer surface 10. Shown are a triangular outer edge with a falling edge towards an outer edge of the spacer surface 10, a rectangular outer edge and a triangular outer edge with a falling edge towards the through bore 20.

Figure 12:
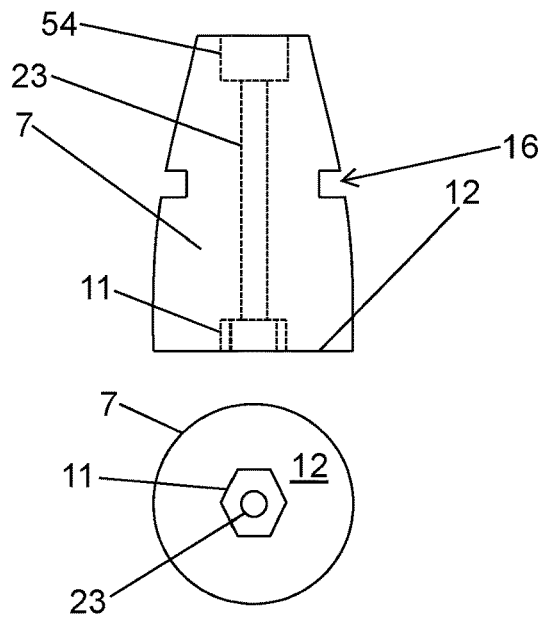
FIG. 12 shows a side view and a bottom view of another example of an abutment.
Figure 13:
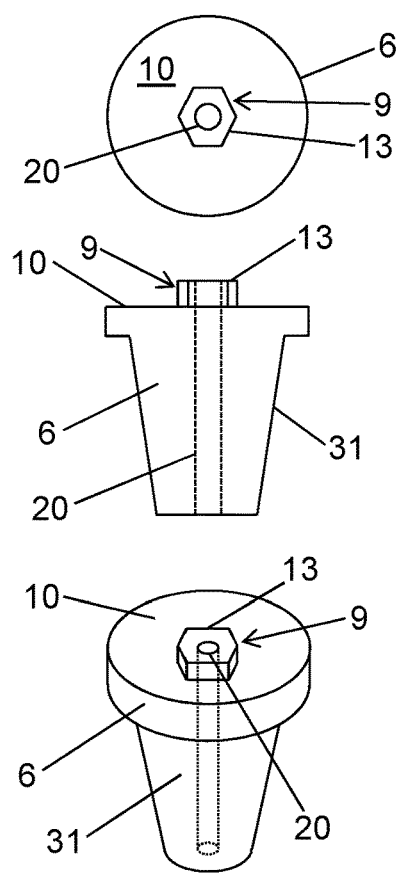
FIG. 13 shows a top view, a side view and a perspective view of a spacer element.

FIG. 12 shows a side view and a bottom view of another example of an abutment 7 having a recess 11 with a polygonal outer edge and FIG. 13 shows a top view, a side view and a perspective view of a spacer element 6 having a polygonal projection 9 which corresponds to the polygonal recess 11 of the abutment 7 according to FIG. 12. The projection 9 is of hexagonal shape and the recess 11 is also of hexagonal shape and slightly bigger than the projection 9. Therefore, the projection 9 can engage into recesses 11 in a form-locked and rotationally locked manner. The hexagonal projection 9 is provided with a sharp cutting edge 13 on top.

Figure 14:
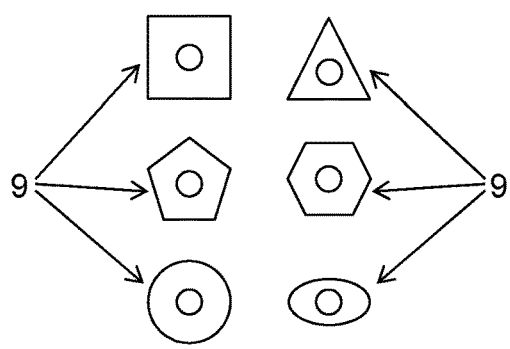
FIG. 14 shows examples of outer edges of projections.

FIG. 14 shows examples of outer edges of projections 9 in top views. Shown are rectangular, triangular, pentagonal, hexagonal, circular and elliptic outer shapes.

Figure 15:
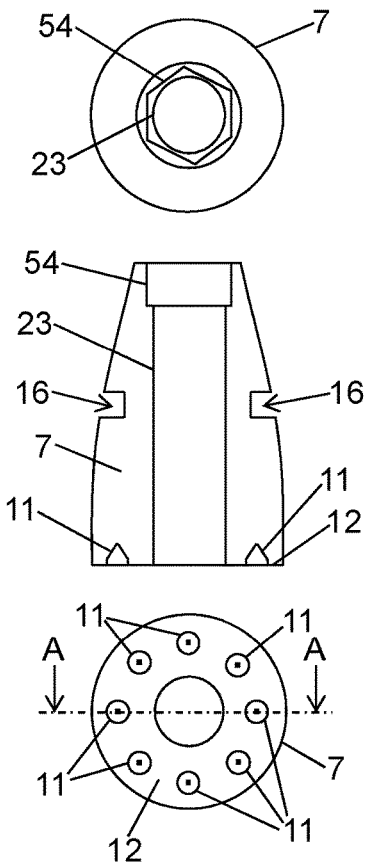
FIG. 15 shows a top view, a sectional side view and a bottom view of another example of an abutment.

FIG. 15 shows a top view, a sectional side view and a bottom view of another example of an abutment 7, wherein the sectional side view shows the cross-section of the abutment 7 along section plane A-A shown in the bottom view. As can be seen in the top view, the tool recess 54 is of hexagonal shape, allowing a tool with a corresponding hexagonal outer shape (e.g. a hexagonal Allen key) to engage with the tool recess 54. The abutment surface 12 has eight recesses 11 to be engaged with projections 9 of a spacer element 6 in order to form a form-locked connection 8 to connect the abutment 7 with the spacer element 6 in a form-locked way. For example, if the abutment 7 shown is to be connected to a spacer element 6 according to FIG. 4 which has four projections 9 only, the abutment 7, due to having eight recesses 11, can be placed onto the spacer element 6 in eight different angular positions relative to the spacer element 6. This facilitates the positioning of the abutment 7 on the spacer element 6, in particular if the abutment 7 is angulated.

Figure 16:
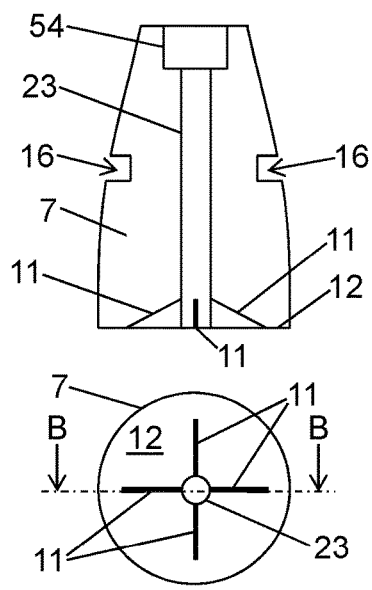
FIG. 16 shows a sectional side view and a bottom view of another example of an abutment.

FIG. 16 shows a sectional side view and a bottom view of another example of an abutment 7, wherein the sectional side view shows the cross-section of the abutment 7 along section plane B-B shown in the bottom view. In this example, the abutment 7 has four slot-shaped recesses 11 which extend from the through hole 23 radially outwards. In the cross-section shown in the sectional side view, the recesses 11 have a triangular outer shape with a falling edge towards an outer edge of the abutment surface 12. The recesses 11 are to be engaged with corresponding ledge-shaped projections 9 on a spacer element 6.

Figure 17:
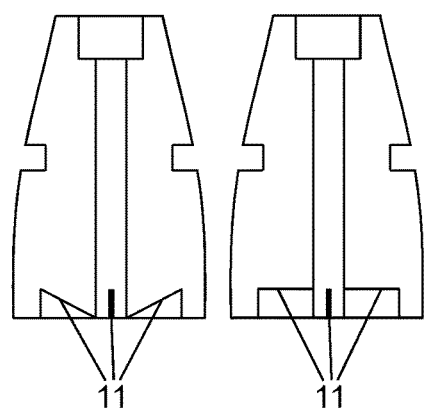
FIG. 17 shows further examples of outer edges of recesses.

FIG. 17 shows further examples of outer edges of recesses 11 in a sectional side view according to the sectional side view of FIG. 16. Shown are a triangular outer edge with a falling edge towards the through hole 23 and a rectangular outer edge.

Figure 18:
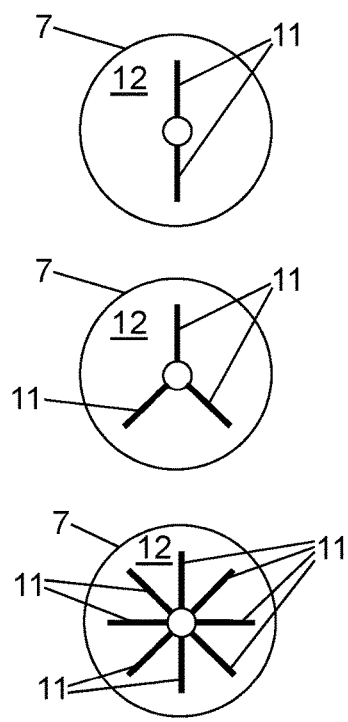
FIG. 18 shows bottom views of three further examples of abutments.

FIG. 18 shows bottom views of three further examples of abutments 7 having two, three and eight slot-shaped recesses 11.

FIG. 19 shows a top view and a side view of the fixing screw 17 according to FIGS. 1, 2 and 3. The screw head 52 has a slot shaped head recess 53 for engagement with a tool like for example a screwdriver. Other commonly used shapes of head recesses 53 are for example a square bore (for engagement with an Allen wrench with a square connector), a hexagonal bore (for engagement with an Allen wrench with a square connector) or a cross recess (for engagement with a cross-headed or Philips-tip screwdriver). For fixing a dental implant system 1 usually a torque of 10-60 Ncm (Newton centimeter) is used. The maximum torque used can for example be defined by using torque screwdriver or torque wrench. Defining a maximum torque can be important, because sometimes implants can be fixed only up to a maximum torque value of 30 Ncm (sometimes even only up to 10 Ncm) in a jawbone due to the structure of the jawbone.

FIG. 20 shows a top view and a side view of another example of a fixing screw 17. In this example, the screw head 52 is of hexagonal shape for engagement with a tool like for example a wrench. In addition, the screw head 52 has a central threaded head bore 58 into which a head screw 59 can be screwed in order to fix a dental prosthesis like e.g. a dental crown at the dental implant system 1.

FIG. 21 shows a top view and a side view of another example of a fixing screw 17. In this example, the screw head 52 has hexagonal head recess 53 for engagement with a tool like for example a corresponding hexagonal Allen key. In addition, the screw head 52 has a central threaded head bore 58 into which a head screw 59 can be screwed.

Figure 22:
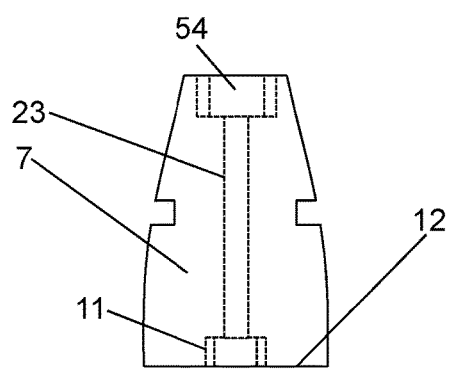
FIG. 22 shows a side view and a top view of another example of an abutment.
Figure 23:
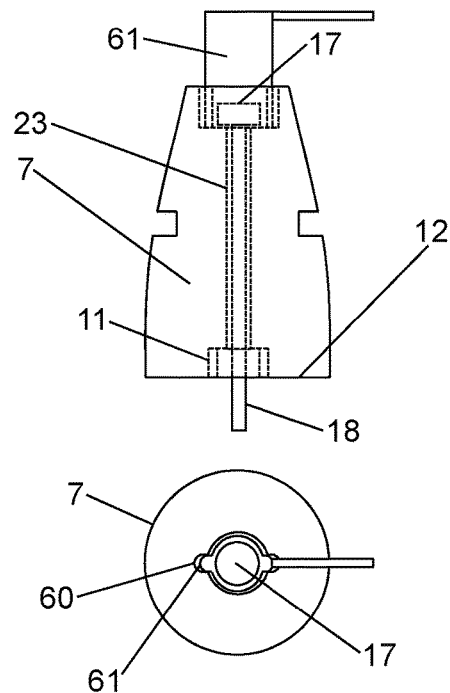
FIG. 23 shows the abutment of FIG. 22 with a fixing sleeve engaged to the abutment in a side view and a top view.

FIG. 22 shows a side view and a top view of another example of an abutment 7 and FIG. 23 shows the abutment 7 of FIG. 22 with a fixing sleeve 61 engaged to the abutment 7 in a side view and a top view. In this example, the tool recess 54 is in the form of a cylindrical cavity with lateral cut-outs 60. According to FIG. 23 a fixing sleeve 61 with an outer shell corresponding to the tool recess 54 is engaged into the tool recess 54 in order to hold the abutment 7 in position during fixing of the dental implant system 1 by screwing the fixing screw 17 into the implant 4. Generally, the tool recess 54 can have various shapes to engage with corresponding fixing devices like e.g. counter torque devices or counter torque wrenches or screwdrivers. For example, the tool recess 54 can have the shape of an internal hexagonal socket (bigger than the screw head 52 of the fixing screw 17) into which a counter torque device with a corresponding outer hexagonal shape can engage.

FIG. 24 shows another example of an abutment 7 and a corresponding spacer element 6. In this example, the abutment 7 has projections 9 projecting from the abutment surface 12 and the spacer element 6 has corresponding recesses 11 formed in the spacer surface 10. The projections 9 of the abutment 7 and the corresponding recesses 11 of the spacer element 6 together form the form-locked connection 8 for connecting the abutment 7 with the spacer element 6 in a form-locked manner. Further, arranged on the spacer surface 10 of the spacer element 6 are thorn-like extensions 25 which in the fitted position are pressed into the film 5 and thus represent a further rotation-preventing means for the film 5.

FIG. 25 shows another example of an abutment 7 and a corresponding spacer element 6. In this example, the abutment 7 has a projection 9 projecting from the abutment surface 12 and also has a recess 11 formed in the abutment surface 12. Similarly, the spacer element 6 has a corresponding recess 11 formed in the spacer surface 10 and also has a corresponding projection 9 projecting from the spacer surface 10. The projections 9 of the abutment 7 and the spacer element 6 and the corresponding recesses 11 of the spacer element 6 and the abutment 7 together form the form-locked connection 8 for connecting the abutment 7 with the spacer element 6 in a form-locked manner. Further, arranged on the abutment surface 12 of the abutment 7 are thorn-like extensions 25 which in the fitted position are pressed into the film 5 and thus represent a further rotation-preventing means for the film 5.

FIG. 26 shows another example of an abutment 7 and a corresponding spacer element 6. In this example, the abutment 7 has projections 9 projecting from the abutment surface 12 and the spacer element 6 has corresponding recesses 11 formed in the spacer surface 10. The projections 9 of the abutment 7 and the corresponding recesses 11 of the spacer element 6 together form the form-locked connection 8 for connecting the abutment 7 with the spacer element 6 in a form-locked manner. In this example, the projections 9 are in the form of ledges projecting from the abutment surface 12 with triangular outer edges with a falling edge towards an outer edge of the abutment surface 12.

FIG. 27 shows another example of an abutment 7 and a corresponding spacer element 6. In this example, the abutment 7 has two projections 9 projecting from the abutment surface 12 and also has two recesses 11 formed in the abutment surface 12. Similarly, the spacer element 6 has two corresponding recesses 11 formed in the spacer surface 10 and also has two corresponding projections 9 projecting from the spacer surface 10. The projections 9 of the abutment 7 and the spacer element 6 and the corresponding recesses 11 of the spacer element 6 and the abutment 7 together form the form-locked connection 8 for connecting the abutment 7 with the spacer element 6 in a form-locked manner. In this example, the projections 9 are in the form of ledges with rectangular outer edges.

FIG. 28 shows a sectional side view and a bottom view of an example of a punch device 40, wherein the sectional side view shows the cross-section of the punch device 40 along section plane C-C shown in the bottom view, as well as a top view and a side view of a spacer element 6 which is a spacer element 6 as shown in FIG. 4. The punch device 40 can be used to punch and press the film 5 onto the spacer element 6 in order to facilitate the arrangement of the film 5 on the spacer element 6 and in order to facilitate the penetration of the projections 9 on the spacer surface 10 of the spacer element 6 through the film 5. In this example, the punch device 40 has an annular punch groove 42 into which the projections 9 of the spacer element 6 can be introduced when the punch device 40 is arranged on top of the spacer element 6 and pressed against the spacer element 6. In addition, the punch device 40 has a punch thorn 41 projecting from the punch device 40 which corresponds to the through bore 20 of the spacer element 6 when the punch device 40 is arranged on and pressed against the spacer element 6 in order to punch the film 5 in the region of the through bore 20. By this, a subsequent insertion of the screw bolt 18 of the fixing screw 17 through the film 5 and the through bore 20 of the spacer element 6 is facilitated. The punch device 40 further has punch device recesses 44 in order to be able to bring a tool into engagement with the punch device 40, like for example a wrench or a handle.

FIG. 29 shows a sectional side view and a bottom view of a further example of a punch device 40, wherein the sectional side view shows the cross-section of the punch device 40 along section plane D-D shown in the bottom view, as well as a top view and a side view of a spacer element 6 which is a spacer element 6 as shown in FIG. 8. In this example, the punch device 40 has a punch space 43 in the form of a cylindrical bore into which the projections 9 of the spacer element 6 which are for example in the form of curved ledges can be introduced when the punch device 40 is arranged on top of the spacer element 6 and pressed against the spacer element 6. In addition, the punch device 40 shown in this example is equipped with a handle 45 in order to facilitate the handling of the punch device 40 or to act as a counter torque when using a screw.

FIG. 30 shows a top view and a side view of another example of a punch device 40. In this example, the film 5 is punched by the screw bolt 18 of the fixing screw 17 and the punch device 40 is pressed against the spacer element 6 by screwing the fixing screw 17 into the implant 4 (which is not shown in this figure). By this, the projections 9 on the spacer element 6 perforate the film 5. In this example, the punch device 40 has a punch device recess 62 in the form of a cylindrical cavity with lateral cut-outs 60. A fixing sleeve 61 with an outer shell corresponding to the recess is engaged into the punch device recess 62 of the punch device 40 in order to hold the punch device 40 in position during punching the film 5 by screwing the fixing screw 17 into the implant 4. Such a punch device 40 can be advantageous in case of a very resistant film 5. Generally, the punch device recess 62 in the punch device 40 can have various shapes to engage with corresponding fixing devices like e.g. counter torque devices or counter torque wrenches or screwdrivers. For example, the punch device recess 62 in the punch device 40 can have the shape of an internal hexagonal socket (bigger than the screw head 52 of the fixing screw 17) into which a counter torque device with a corresponding outer hexagonal shape can engage.

FIG. 31 shows another example of a punch device 40 with corresponding fixing sleeve 61. In this example, the punch device recess 62 extends further towards the spacer element 6. In particular, the punch device recess 62 can be of such depth that the fixing screw 17 can be introduced so far that there is a defined distance between an end face of the punch device 40 that faces towards the spacer element 6 and the screw head 52, wherein this defined distance can be the same distance as when the fixing screw 17 is introduced into the abutment 7 and screwed into the threaded bore 19 of the implant 4.

Figure 32:
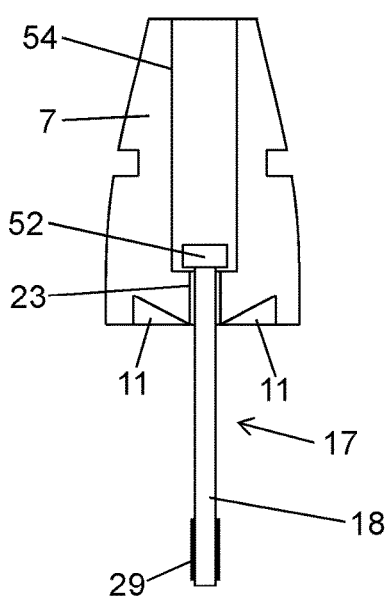
FIG. 32 shows a sectional side view of another example of an abutment.

FIG. 32 shows a further example of an abutment 7 which is similar to one of the abutments 7 shown in FIG. 17. In the example of FIG. 32, when compared with FIG. 17, the tool recess 54 extends further towards the abutment surface 12. In particular, the tool recess 54 can be of such depth that the fixing screw 17 can be introduced so far that there is a defined distance between the abutment surface 12 and the screw head 52, wherein this defined distance can be the same distance as the distance between a face end of a punch device 40 and the screw head 52 (see, e.g., the punch device 40 shown in FIG. 31). By this, the length of the screw bolt 18 of the fixing screw 17 only needs to be adapted to the height of the spacer element 6 used and not also to the specific abutment 7 used and one and the same fixing screw 17 can be used for perforating the film 5 with the punch device 40 and subsequently for fixing the dental implant system 1.

Figure 33:
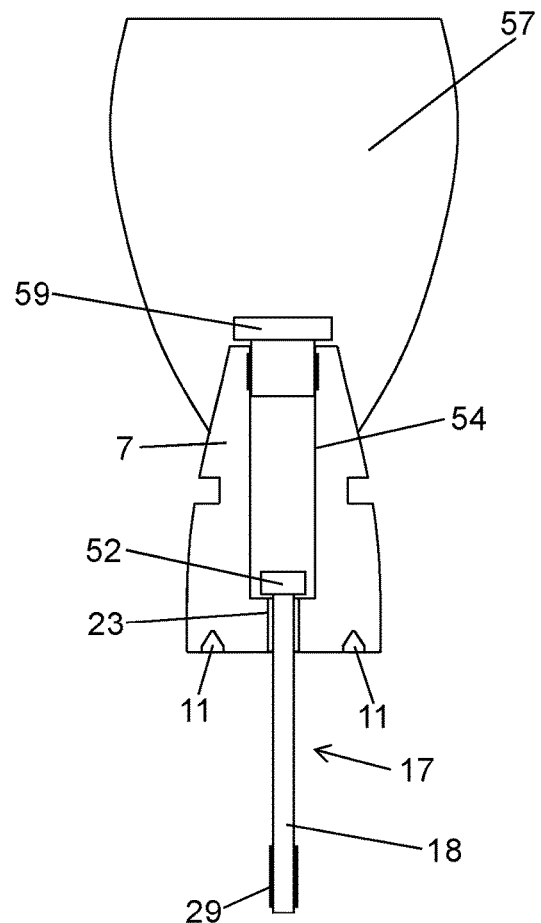
FIG. 33 shows the abutment of FIG. 32 with a dental prosthesis arranged thereon.

FIG. 33 shows the abutment of FIG. 32 with a dental prosthesis 57 arranged on the abutment 7. In the shown example, the dental prosthesis 57 is screwed onto the abutment 7 by means of a threaded head screw 59 which is screwed in to the threaded tool recess 54 of the abutment 7.

Figure 34:
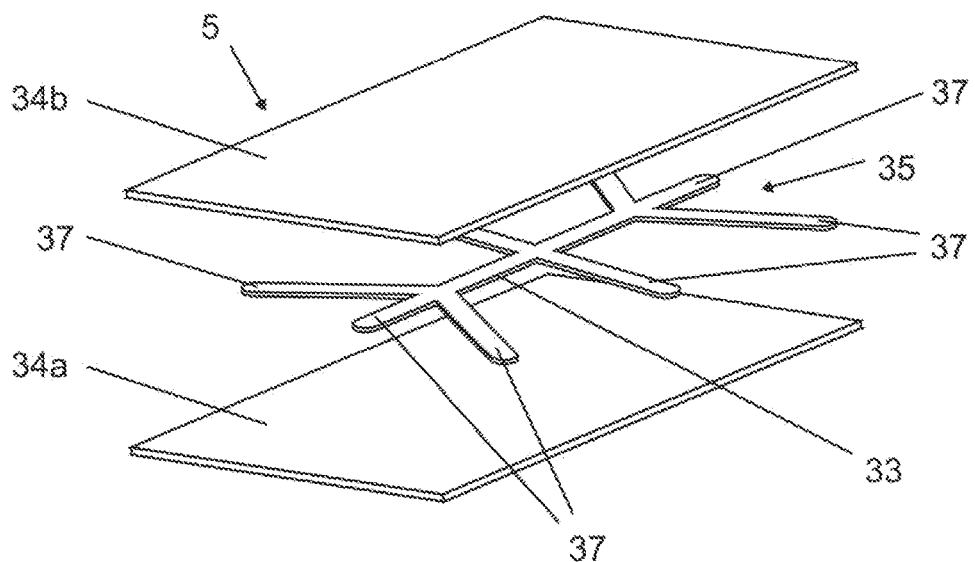
FIG. 34 shows an exploded perspective view of an embodiment of a multi-layer film.

FIG. 34 shows an exploded perspective view of a proposed pre-bonded multi-layer film 5. The film 5 includes a forming layer 33 and two cover layers 34a and 34b. The forming layer 33 is stiffer than the cover layers 34a and 34b and has a shape structure 35. The shape structure 35 includes a plurality of strut-shaped forming elements 37 which serve to form the film 5 over a bone defect site 2 (this is not shown here), wherein the film 5 can be well shaped by the forming elements 37 to a jawbone 3 which is still present at the bone defect site 2. The shape structure 35 is overall of a substantially grid-shaped configuration and thus permits the provision of any surface shapes for the film 5 so that, in conjunction with a bone defect site 2, it is possible to form any desired cavity shapes between the film 5 and the bone defect site 2.

The forming layer 33 and the cover layers 34a and 34b respectively comprise a bioresorbable material so that the film 5 as a whole is substantially complete resorbable in the body. By virtue of the provision of two cover layers 34a and 34b, between which the forming layer 33 is embedded, it is possible to control in particular the resorption speed and mechanical strength of the forming layer 33.

The cover layers 34a and 34b can be for example bioresorbable collagen membranes which on the one hand by virtue of their softness can well cover a bone defect site 2 and which on the other hand can be well glued to a gum 55 surrounding the bone defect site 2 so as to afford good sealing for the bone defect site 2.

The forming layer 33 can for example comprise a bioresorbable polymer material or copolymer material. In particular the forming layer 33 can include for example about 82% L-lactic acid and about 18% glycolic acid. Such a choice of material affords a forming layer 33 which is substantially stable in shape and which is adapted to be mechanically, thermally and/or chemically deformable for shaping to a bone defect site 2, wherein after such deformation the forming layer 33 is substantially stable in shape again. By virtue of the stiffness and stability in respect of shape of the forming layer 33 therefore a cavity for bone regeneration can be created between the film 5 and a bone defect site 2 and also maintained for the period of bone regeneration.

Figure 35:
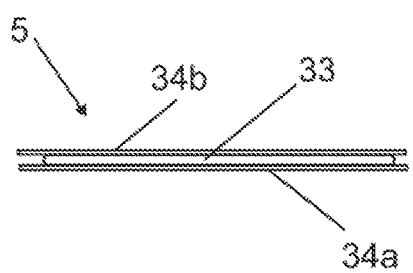
FIG. 35 shows a side view of the multi-layer film of FIG. 34, FIGS. 36-40 show plan views of various embodiments of multi-layer films.

FIG. 35 shows a side view of the pre-bonded multi-layer film 5 as shown in FIG. 34.

Figure 36:
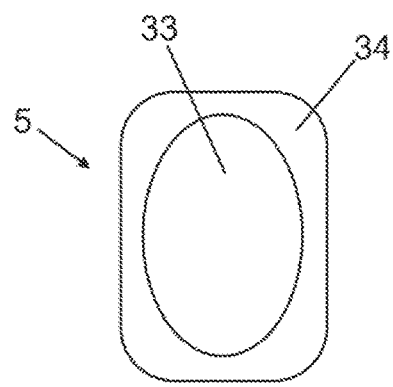

FIG. 36 shows a plan view of a further variant of the proposed film 5 which in this example is of a double-layer nature and includes a forming layer 33 and a cover layer 34. Both the forming layer 33 and also the cover layer 34 are substantially flat. The film 5 can be cut to size as desired in order, depending on the respective situation of use, to permit good shaping to a bone defect site 2.

Figure 37:
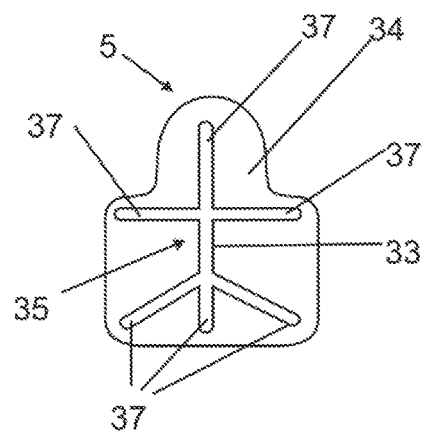
Figure 38:
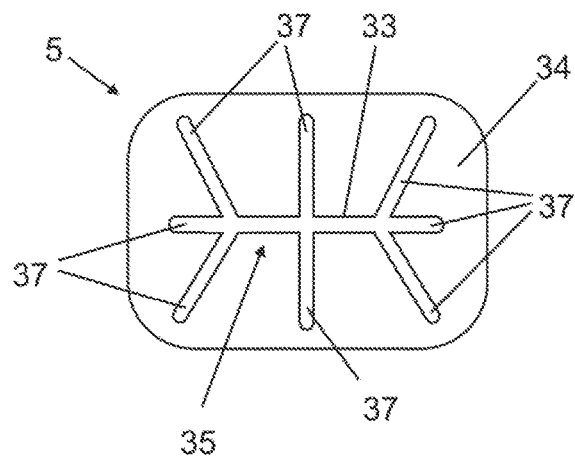

FIGS. 37 and 38 show two further embodiments of a proposed two-layer film 5 with different outside contours in respect of the cover layer 34 and different shape structures 35 of the forming layer 33.

Figure 39:
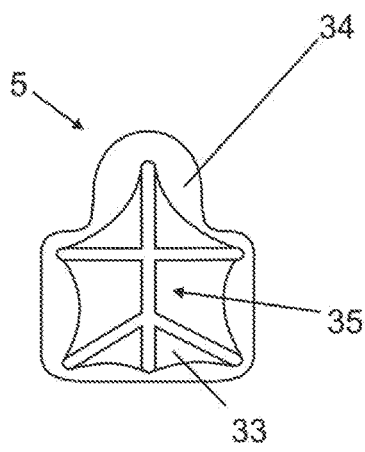
Figure 40:
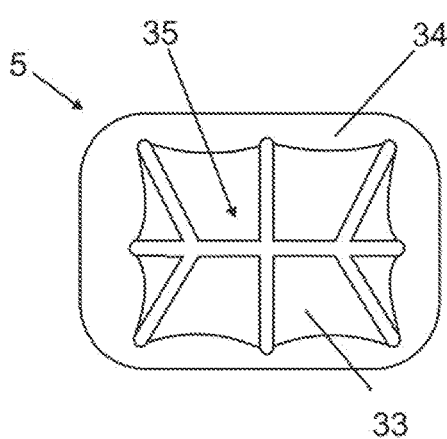

FIGS. 39 and 40 show further example of proposed films 5, wherein, in the examples shown here, the forming layer 33 was respectively applied in the form of a gel to the cover layer 34 and subsequently hardened. The forming layers 33 shown here each include a shape structure 35 which for example was achieved by more gel being applied in the regions of the structure 35 so that the forming layers 33 are of differing layer thicknesses. In the region of a forming structure 35 a forming layer 33 is of a respectively greater layer thickness than in the other regions of the forming layer 33.

FIGS. 41 through 48 each show an exploded perspective view of further respective embodiments of a proposed film 5. The side 39 of a film 5, that faces downwardly in the respective Figures, is in this case the side 39 of the film 5, that is to face towards a bone defect site 2.

Figure 41:
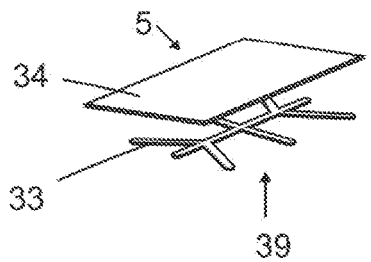
FIGS. 41-48 show exploded perspective views of a number of embodiments of multi-layer films.
Figure 42:
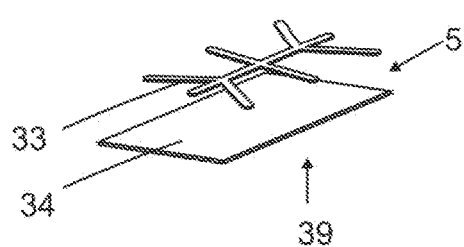
Figure 43:
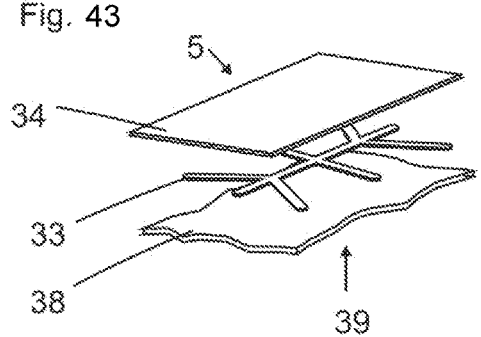
Figure 44:
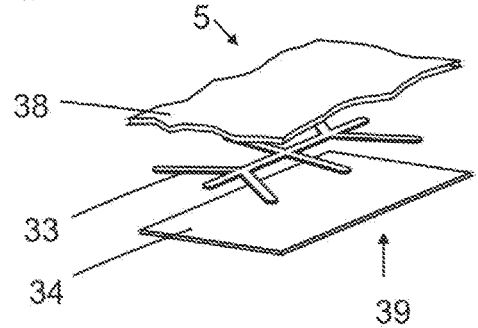
Figure 45:
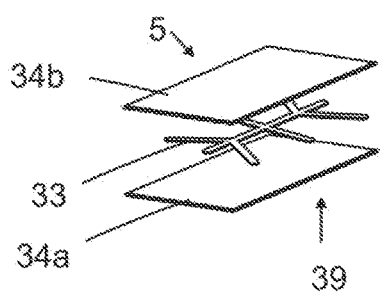
Figure 46:
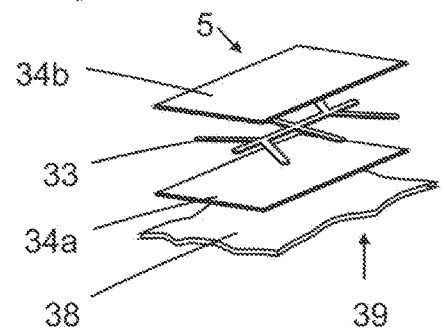
Figure 47:
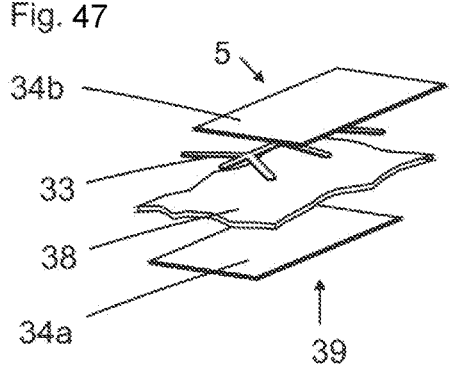
Figure 48:
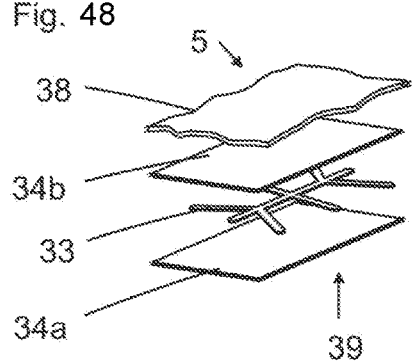

The examples of FIG. 41 and FIG. 42 are of a two-layer structure and respectively include a forming layer 33 and a cover layer 34, the forming layer 33 occupying a smaller surface area than the cover layer 34. The examples in FIG. 43 and FIG. 44 are of a three-layer structure and, besides a forming layer 33 and a cover layer 34, respectively include a carrier layer 38 to which substances like for example drugs, growth factors and/or other substances for protecting and promoting healing and bone formation can be applied.

The examples of FIG. 45 through FIG. 48 each have a forming layer 33 and two cover layers 34a and 34b, the forming layer 33 occupying a smaller surface area than the cover layers 34a and 34b. The examples of FIGS. 46 through 48 each additionally have a carrier layer 38 which can be provided with suitable substances (as described above in relation to FIG. 43 and FIG. 44).

The invention claimed is:

1. A dental implant system for bone regeneration of a bone defect site of a jawbone, the dental implant system including:
   an implant which is to be anchored in the jawbone;
   a film for covering over the bone defect site and the implant;
   a spacer element which, in a fitted position of the dental implant system, is to be arranged between the implant and the film; and
   an abutment,
   wherein, in the fitted position of the dental implant system:
   the film is clamped between the spacer element and the abutment;
   the spacer element and the abutment are connected by a form-locked connection;
   the spacer element is configured to level out different levels between a top of the implant and an edge of the bone defect site; and
   a top surface of the spacer element is configured to be at an opening of the bone defect site such that: (i) the film rests on the top surface of the spacer element; and (ii) the film extends across the bone defect site.

2. The dental implant system as set forth in claim 1, wherein the form-locked connection is rotationally locked.

3. The dental implant system as set forth in claim 1, wherein the form-locked connection is configured such that:
   the spacer element has at least one projection projecting from the top surface of the spacer element that faces towards the film in the fitted position of the dental implant system, and the abutment has at least one recess in an abutment surface of the abutment that faces towards the film in the fitted position of the dental implant system; or
   the abutment has least one projection projecting from the abutment surface, and the spacer element has at least one recess in the top surface of the spacer element; and
   wherein, in the fitted position of the dental implant system, the at least one recess corresponds to the at least one projection such that the at least one projection projects through the film and into the at least one recess.

4. The dental implant system as set forth in claim 3, wherein the at least one projection has at least one sharp edge or tip in order to facilitate penetration of the at least one projection through the film.

5. The dental implant system as set forth in claim 3, wherein the at least one projection is a pin or ledge.

6. The dental implant system as set forth in claim 3, wherein the at least one projection has a conical, tapered, rectangular or triangular outer shape.

7. The dental implant system as set forth in claim 3, wherein the at least one projection includes a plurality of projections.

8. A set comprising;
   the dental implant system as set forth in claim 3; and
   a punch device for punching and pressing the film onto the spacer element in order to facilitate arrangement of the film on the spacer element and in order to facilitate penetration of the at least one projection through the film,
   wherein:
   the punch device has an annular punch groove or a punch space defining a cylindrical bore; and
   the at least one projection can be introduced into the annular punch groove or the punch space when the punch device is arranged on top of the spacer element and pressed against the spacer element.

9. The dental implant system as set forth in claim 1, wherein, in the fitted position of the dental implant system, the implant and the spacer element are connected by a form-locked spacer connection.

10. The dental implant system as set forth in claim 9, wherein the form-locked spacer connection is rotationally locked.

11. The dental implant system as set forth in claim 1, wherein the abutment has at least one tool reception.

12. The dental implant system as set forth in claim 1, further comprising:
   a fixing screw for positionally fixing the film relative to the implant,
   wherein, in the fitted position of the dental implant system:
   a screw bolt of the fixing screw projects through the abutment, the film and the spacer element; and
   the screw bolt is screwed into a threaded bore in the implant.

13. The dental implant system as set forth in claim 12, wherein:

the spacer element is configured to pass the screw bolt therethrough and has a through bore of a bore diameter which is larger than an outside diameter of the screw bolt; and the abutment is configured to pass the screw bolt therethrough and has a through hole of a hole diameter which is larger than the outside diameter of the screw bolt.

14. The dental implant system as set forth in claim 1, wherein at least one extension is on at least one of: (i) the top surface of the spacer element that faces towards the film in the fitted position of the dental implant system; and (ii) an abutment surface of the abutment that faces towards the film in the fitted position of the dental implant system.

15. The dental implant system as set forth in claim 14, wherein the at least one extension is of a thorn configuration.

16. The dental implant system as set forth in claim 1, wherein the film is at least partially resorbable.

17. The dental implant system as set forth in claim 16, wherein the film is completely resorbable.

18. The dental implant system as set forth in claim 1, wherein the film includes:

a shaping forming layer for shaping the film to the bone defect site; and at least one cover layer for covering the bone defect site, wherein the shaping forming layer and the at least one cover layer are at least partially resorbable.

19. The dental implant system as set forth in claim 18, wherein the film is a pre-bonded multi-layer film.

20. The dental implant system as set forth in claim 18, wherein the shaping forming layer and the at least one cover layer are completely resorbable.

21. A set comprising:

the dental implant system as set forth in claim 1; and a punch device for punching and pressing the film onto the spacer element in order to facilitate arrangement of the film on the spacer element.

22. The dental implant system as set forth in claim 21, wherein the punch device has a punch thorn projecting from the punch device or a recess for introducing a screw bolt of a fixing screw in order to punch the film when the punch device is arranged on and pressed or screwed against the spacer element.

23. The dental implant system as set forth in claim 1, wherein the top surface of the spacer element is configured to be at the opening of the bone defect site such that the top surface of the spacer element is at a same level as the edge of the bone defect site.

* * * * *